(12) United States Patent
Schoch

(10) Patent No.: US 6,406,495 B1
(45) Date of Patent: Jun. 18, 2002

(54) GLENOID PROSTHESIS AND A MODULAR SYSTEM WITH GLENOID PROSTHESES

(75) Inventor: Roland Schoch, Baar (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/464,329

(22) Filed: Dec. 15, 1999

(30) Foreign Application Priority Data

Dec. 22, 1998 (EP) .............................................. 98811255

(51) Int. Cl.[7] .................................................. A61F 2/28
(52) U.S. Cl. .................................. 623/19.13; 623/19.11
(58) Field of Search ........................... 623/19.11, 19.12, 623/19.13, 18.11, 18.12, 19.14, 22.32, 22.34, 22.35, 22.37, 22.38

(56) References Cited

U.S. PATENT DOCUMENTS

| 4,978,355 A | * | 12/1990 | Frey et al. ................ 623/23.54 |
| 5,032,132 A | * | 7/1991 | Matsen, III et al. ..... 623/19.11 |
| 5,702,447 A | * | 12/1997 | Walch et al. ............ 623/19.11 |

FOREIGN PATENT DOCUMENTS

| EP | 0 581 667 A1 | 2/1994 | |
| EP | 0581667 | * 2/1994 | .................. 623/19 |
| FR | 2 579 454 | 10/1986 | |

\* cited by examiner

*Primary Examiner*—Cary O'Connor
(74) *Attorney, Agent, or Firm*—Townsend and Townsend and Crew LLP

(57) ABSTRACT

A glenoid prosthesis including a bearing shell, the reverse side of which has a plurality of anchoring pins which are arranged to one another. At least one anchoring pin has a coupling element, and at least one sleeve with a fitting securable coupling element and an outer anchoring structure is provided in order to selectively enable a cementing in of the anchoring pin or a mechanical hammering in of the pin together with the sleeve which is fixed to it.

11 Claims, 2 Drawing Sheets

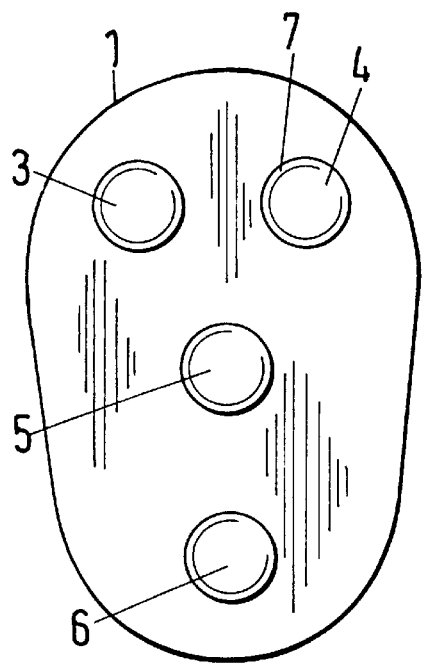
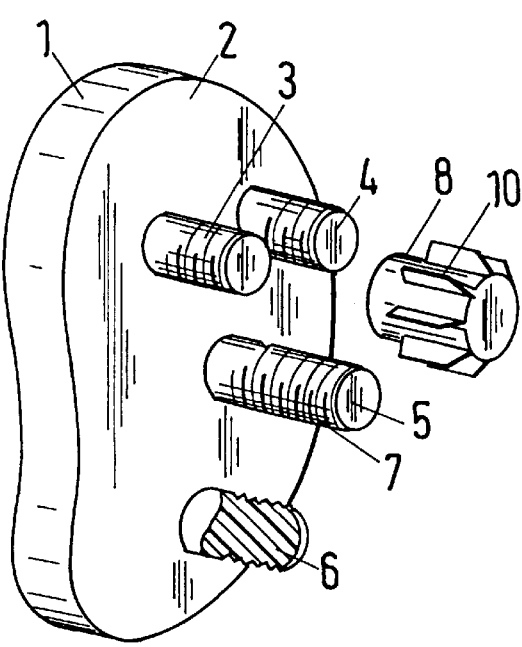
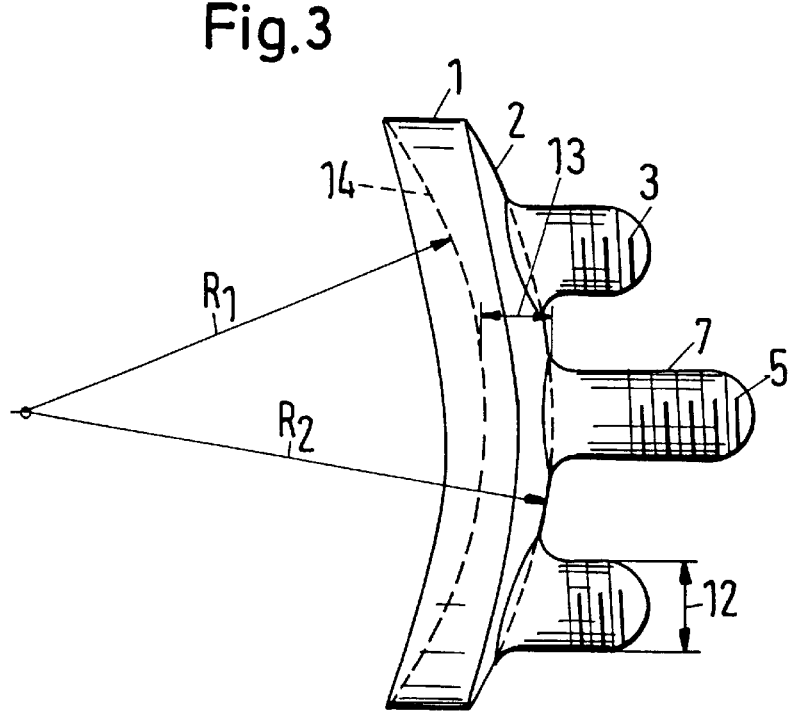

GLENOID PROSTHESIS AND A MODULAR SYSTEM WITH GLENOID PROSTHESES

BACKGROUND OF THE INVENTION

1. Field of the Invention

The invention relates to a glenoid prosthesis comprising a plastic bearing shell with a plurality of integral anchoring pins, which are arranged parallel to one another at its reverse side.

2. Description of the Prior Art

The operation technique and the material used are described in detail in a brochure: "Schulter-Endoprothese zementiert", 1998 edition of Sulzer Orthopedics Ltd., CH-6340 Baar. A glenoid prosthesis with four pins on the reverse side is shown which is cemented in after the milling and boring of the natural glenoid.

SUMMARY OF THE INVENTION

The object of the present invention is to be able to insert a glenoid prosthesis of this kind in a wider spectrum of applications. This object is achieved by the present invention in that at least one anchoring pin has a thread as a coupling element, and in that a metal sleeve with protruding longitudinal ribs is solidly screwable to that one anchoring pin for a mechanical hammering in of the sleeve into an undersized bone hole.

This design of the glenoid prosthesis brings about a plurality of advantages. It permits the prosthesis to be selectively cemented in or to be anchored directly in the bore without cement after the securing of sleeves with anchoring structures. In the cementing in, the coupling structure at the pins has the advantage that projections and recessions are present for the cement jacket and that no overloading takes place since cement can flow back into depressions. In the hammering in without cement a sleeve material which is suitable for the growing in and an anchoring structure on the sleeve which is suitable for the hammering in can be used.

Other embodiments of the present invention provide advantages. It is advantageous if the pins have an outer thread as a coupling element and the sleeves have an inner thread as a fitting coupling element. Bayonet locks are likewise possible. In addition it is advantageous if all pins are provided with equally large thread diameters independently of the size of the bearing shells since only one additional part, the sleeve, need be taken up into the bearing holder. Furthermore, a bearing shell with pins of a material which has good sliding properties can be chosen without it being necessary for the anchoring to suffer thereby. A construction of plastic in the form of a bearing shell of polyethylene combined with metallic sleeves of a titanium ally brings about a good anchoring. This can be improved if knife-like ribs in the longitudinal direction are distributed over the periphery of the sleeve. On the one hand, the support surface is enlarged and, on the other hand, the bone material is encouraged to grow in. Furthermore, the growing in of bone matter can be improved if the reverse side of the bearing shell is provided with a metal mesh which for example consists of a titanium alloy.

A further advantage results if the orthopedist can still make the decision, after the boring of the bores for the anchoring pins, in accordance with the state of the bone found, whether he wishes to cement or to hammer in without cement. This is achieved in that the sleeve has such a low wall thickness that the bore diameter, which corresponds to a desired thickness of the cement jacket during the cementing, at the same time also forms the desired bore diameter for the direct hammering in of sleeves with an anchoring structure. That is, the anchoring structure is designed in such a manner relative to the pin that the bore diameter is less than the outer diameter over the anchoring structure and lies in the vicinity of the outer diameter of the actual sleeve.

BRIEF DESCRIPTION OF THE DRAWINGS

FIG. 1 schematically illustrates the view of a bearing shell with threaded pins and a sleeve with longitudinal ribs which can be screwed on;

FIG. 2 schematically illustrates a view of the bearing shell of FIG. 1 from the reverse side;

FIG. 3 schematically illustrates a side view of the bearing shell of FIG. 1;

DETAILED DESCRIPTION OF SPECIFIC EXEMPLARY EMBODIMENTS

Figure 4:
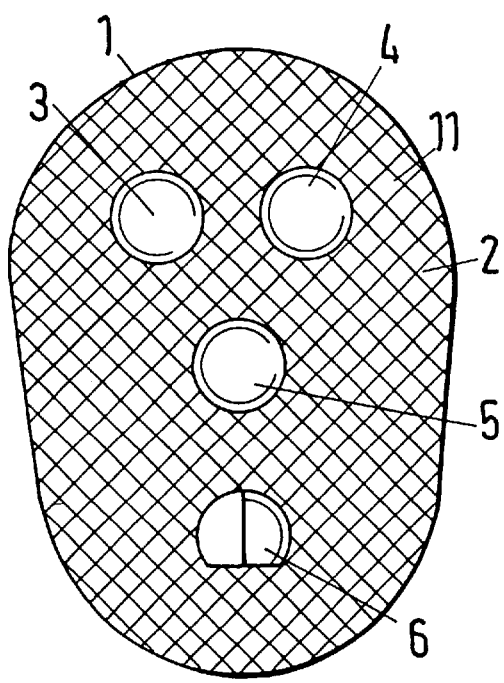
FIG. 4 schematically illustrates the rear view of a bearing shell which is additionally provided at its reverse side with a metal mesh.

The figures show a glenoid prosthesis with a bearing shell 1, the reverse side 2 of which has a plurality of anchoring pins 3, 4, 5, 6 which are arranged parallel to one another. At least one anchoring pin has a coupling element 7 and at least one sleeve 8 with a fitting securable coupling element 9 and an outer anchoring structure 10 is provided in order to selectively enable a cementing in of the anchoring pin or a mechanical hammering in of the pin together with the sleeve which is fixed to it.

In FIGS. 1, 2 and 3 a bearing shell 1 is shown, the bearing surface 14 of which and the reverse side 2 of which are sections of spherical surfaces $R_1$, $R_2$ with a common center. The material of the bearing shell 1 is a UHMW polyethylene and the wall thickness 13, which represents the radius difference $R_2 - R_1$, corresponds to an amount of about 5.5 mm. Wall thicknesses with values between 3 and 7 mm are conceivable with other materials, with the goal therein consisting in achieving as low a wall thickness as possible while retaining a sufficient bearing function and bearing stability since the natural glenoid must be milled in by about this amount if the ligaments are to be tensioned to the same extent after the insertion of the artificial bearing shell.

Four anchoring pins 3, 4, 5, 6 project on the reverse side 2 of the bearing shell and are in each case provided with an outer thread 7 with a thread diameter 12. Pins 3 and 4 are horizontally arranged and pins 5 and 6 vertically arranged corresponding to the securing possibilities at a natural glenoid, with it still being necessary to rotate the bearing shell by 180° for the securing at a person standing erect. The threaded pins 3, 4, 5, 6 are in this case connected in a single piece to the bearing shells and are arranged parallel to one another in order to be able to insert them together in suitably pre-bored bores. The outer thread diameter 5 is the same for all pins. Corresponding to the thickness of a natural glenoid the middle pin 5 projects further forward for the anchoring. The bearing surface 14 of the bearing shell 1 is provided with sufficient surface quality and precision of shape for artificial joints.

A bearing shell of this kind can be pressed directly in with its pins into bores at a natural glenoid which are filled with bone cement. The bone cement which wells forth over the bearing shell is brushed off and the bearing shell is held in place until the bone cement has hardened. During the pressing in of the pins the threads which are placed therein help in the ventilation of enclosed air bubbles since the bore cement does not wet immediately down to the thread base. After the hardening the thread surfaces form clearly defined support surfaces for the transmission of force in the direction of the pins.

Should the operator after the boring of the reception holes in the natural glenoid be of the opinion that the bone substance is stable enough for a direct anchoring, then he can screw the metallic sleeves 8 which belong to the modular system onto the threaded pins, 3, 4, 5, 6 and hammer them in with the bearing shell without bone cement. The wall thickness of the sleeve 8 is executed to be small in order that the bores can be used in the natural glenoid (not shown here) selectively for a direct anchoring of the sleeves 8 or for an anchoring of the pins with bone cement. The sleeves 8 are closed at their front ends and have knife-like longitudinal ribs distributed over the periphery which dig into the bone tissue during the hammering in. The primary securing arises in this case through the frictional forces at the ribs 10 and the sleeves 8. Pure titanium or body compatible titanium alloys are advantageous as a metal for the sleeves 8.

Figure 5:
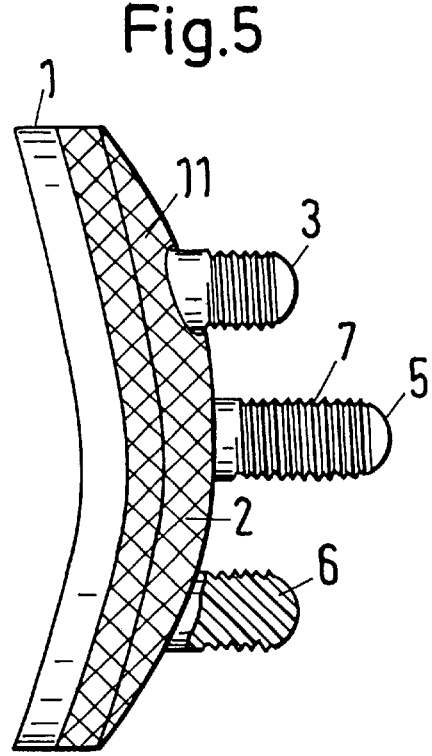
FIG. 5 schematically illustrates a side view of the bearing shell of FIG 4.
Figure 6:
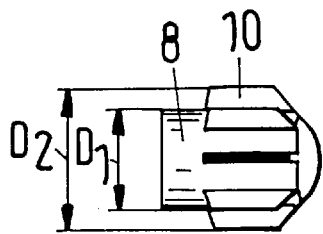
FIG. 6 schematically illustrates a side view of a sleeve with anchoring ribs.
Figure 7:
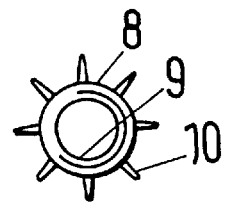
FIG. 7 schematically illustrates a front view showing the threaded bore of the sleeve in FIG. 6.

In the example of FIGS. 4 and 5 a bearing shell 1 of polyethylene is provided with a metallic mesh 11 on its reverse side 2. A mesh which is rounded at its outer edge is heated and pressed on at the reverse side 2 of the bearing shell 1. The metal mesh 11 penetrates partly into the polyethylene and individual wires of the mesh are enclosed by the melted polyethylene in order to achieve an anchoring over the entire surface. If the bearing pin is not to be damaged in this procedure, one possibility consists in providing the metal mesh 11 with cut-outs and securing the pins 3, 4, 5, 6 of polyethylene later at the reverse side 2 by friction welding at the bearing shell 1. Another possibility consists in placing a protective sleeve of a poor heat conductor on the pins for the duration of the joining of the bearing shell 1 and the metallic mesh 11. In addition to the selectively insertable sleeves 8 a bearing shell of this kind has the advantage that a structure which is suitable both for securing with bone cement and also for a direct growing in in the bone is attached to the reverse side 2. FIGS. 6 and 7 show a sleeve 8 in a side view from the rear. The longitudinal ribs 10, which are formed in the shape of knives, are uniformly distributed over the periphery. Bore gauges are provided for the bearing shells. The bores which are produced in the bone with bore gauges have a diameter $D_2 > d \geq 0.9 D_1$, with the diameter $D_2$ being measured over the ribs 10 and the diameter $D_1$ corresponding to the outer diameter of the sleeve body. At the same time this diameter d produces a layer thickness of bone cement between the bore and the pins 3, 4, 5, 6 which is aimed for during the cementing in. The front side of the sleeve 8 is rounded in the shape of a bullet.

What is claimed is:

1. A glenoid prosthesis comprising a plastic bearing shell including a plurality of integral anchoring pins that are arranged parallel to one another at a reverse side of the bearing shell, wherein at least one anchoring pin has a thread element and a corresponding metal sleeve that is preoperative solidly screwable to the at least one anchoring pin, and wherein the corresponding metal sleeve is provided with protruding longitudinal ribs for a mechanical hammering in of the metal sleeve into an undersized bone hole.

2. A prosthesis in accordance with claim 1, wherein all anchoring pins are provided with outer threads.

3. A prosthesis in accordance with claim 1, wherein the bearing shell and the pins consist of polyethylene.

4. A prosthesis in accordance with claim 1, wherein each metal sleeve is closed at a front end and consists of a titanium alloy.

5. A prosthesis in accordance with claim 1, wherein each metal sleeve has longitudinal ribs which are equally distributed over their periphery.

6. A prosthesis in accordance with claim 1, wherein the longitudinal ribs are designed in the manner of knives.

7. A prosthesis in accordance with claim 1, wherein with the exception of the anchoring pins, the reverse side of the bearing shell has a metallic mesh.

8. A prosthesis in accordance with the claim 1, wherein the anchoring pins became integral to the shell through friction welding.

9. A prosthesis in accordance with claim 1, wherein the bearing surface of the bearing shell and the reverse side of the bearing shell are sections of spherical surfaces, and wherein the bearing shell has a wall thickness between 3 mm and 7 mm.

10. A modular system comprising glenoid prosthesis, each prosthesis comprising a plastic bearing shell including a plurality of integral anchoring pins that are arranged parallel to one another at a reverse side of the bearing shell, wherein at least one anchoring pin has a thread element and a corresponding metal sleeve that is preoperative solidly screwable to the at least one anchoring pin, and wherein the corresponding metal sleeve is provided with protruding longitudinal ribs for a mechanical hammering in of the sleeve into an undersized bone hole, the modular system consisting of bearing shells with different outer dimensions, wherein the thread diameter of the pins are equally large for all bearing shells in order to be able to manage with one sleeve size.

11. A modular system in accordance with claim 10, wherein bore gauges are provided for the bearing shells, the guide diameter of which is furnished for borers with diameter $D_2 > d \geq 0.9 D_1$, with diameter $D_2$ corresponding to the diameter which is measured over the ribs and the diameter $D_1$ corresponding to the diameter over the sleeve body.

* * * * *